United States Patent
Okada et al.

Patent Number: 5,922,709
Date of Patent: Jul. 13, 1999

[54] ANTIFUNGAL COMPOSITION

[75] Inventors: Hiromasa Okada; Masao Nagashima; Seigou Kamiya; Katsuhisa Kojiri; Hiroyuki Suda, all of Tsukuba, Japan

[73] Assignee: Banyu Pharmaceutical Co., Ltd., Tokyo, Japan

[21] Appl. No.: 09/068,116

[22] PCT Filed: Nov. 15, 1996

[86] PCT No.: PCT/JP96/03353

§ 371 Date: May 6, 1998

§ 102(e) Date: May 6, 1998

[87] PCT Pub. No.: WO97/18821

PCT Pub. Date: May 29, 1997

Related U.S. Application Data

[30] Foreign Application Priority Data

Nov. 20, 1995 [JP] Japan ................................ 7-325068

[51] Int. Cl.$^6$ .................... A61K 31/71; A61K 31/35; C07D 473/18
[52] U.S. Cl. .................... 514/241; 514/242; 514/245; 514/252; 514/396; 514/399; 514/451; 514/454; 514/455
[58] Field of Search .................... 514/241, 242, 514/245, 252, 396, 399, 451, 454, 455

[56] References Cited

PUBLICATIONS

Natural Product Letters, 1995, vol. 7, "Xylarin, an Antifungal Xylaria Metabolite with an Unusual Tricyclic Uronic Acid Moiety", G. Schneider, et al. p. 309–316.

The Journal of Antibiotics, 1995, vol. 48, No. 10, "SCH57404, an Antifungal Agent Possessing the Rare Sodaricin Skeleton and a Tricyclic Sugar Moiety", Stephen J. Coval, et al. p. 1171–1172.

*Primary Examiner*—Frederick Krass
*Attorney, Agent, or Firm*—Oblon, Spivak, McClelland, Maier & Neustadt, P.C.

[57] ABSTRACT

An antifungal composition, containing a synergistic mixture, containing the compound of the formula (I):

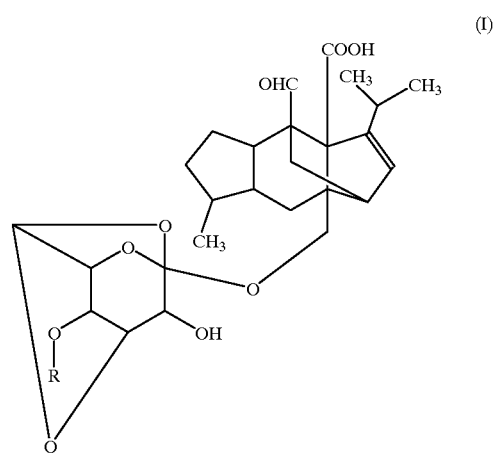

wherein R is acetyl or lower alkyl; or a pharmaceutically acceptable salt thereof; and an azole antifungal agent selected from the group consisting of an imidazole compound and a triazole compound, as an active ingredient.

10 Claims, No Drawings

ANTIFUNGAL COMPOSITION

TECHNICAL FIELD

The present invention relates to an antifungal composition which is useful in the pharmaceutical field and which is more specifically novel.

BACKGROUND ART

In the field of antifungal agents, many compounds have already been practically used as pharmaceutical products. However, their effects are not necessarily adequate against various types of harmful fungi. Further, emergence of resistant strains against these pharmaceutical agents, particularly resistant strains against azole type antifungal agents which are frequently used, has become a clinically serious problem. Accordingly, it has been desired to develop a pharmaceutical agent effective against such harmful fungi and resistant strains.

DISCLOSURE OF THE INVENTION

It is an object of the present invention to provide a novel antifungal agent which is capable of satisfying the above demand. Namely, it is a problem to be solved by the present invention to present a pharmaceutical agent which provides antifungal effects also against various harmful fungi and resistant strains against which conventional antifungal agents can not provide adequate effects.

The present inventors have conducted extensive studies to solve the above problem and as a result, have found that by combining a compound represented by the general formula (I) or its pharmaceutically acceptable salt, and an azole type antifungal agent, such a composition has excellent antifungal activities, and the present invention has been accomplished.

Namely, the present invention relates to an antifungal composition comprising a compound represented by the general formula (I):

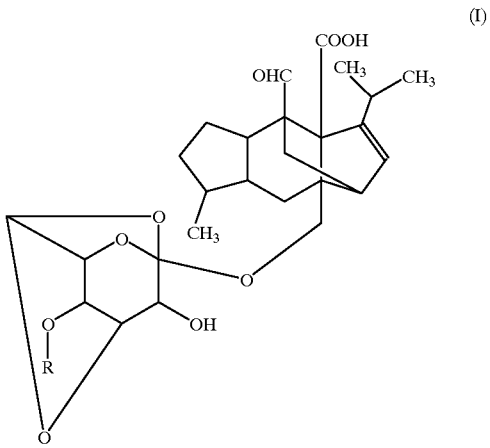

(I)

wherein R is an acetyl group or a lower alkyl group, or its pharmaceutically acceptable salt, and an azole type antifungal agent, as active ingredients.

The symbols and terms used in this specification will be described.

The lower alkyl group means a $C_{1-6}$ linear or branched alkyl group, and, for example, a methyl group, an ethyl group, a propyl group, an isopropyl group, a butyl group, a sec-butyl group, a tert-butyl group, a pentyl group or a hexyl group may be mentioned. Particularly preferred is a methyl group.

The pharmaceutically acceptable salt of the compound represented by the general formula (I) may, for example, be a salt such as a base-addition salt at the carboxyl group.

Such a base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

Among the compounds represented by the general formula (I), a compound wherein R is an acetyl group, will be hereinafter referred to as BE-31405.

BE-31405 is a compound found by the present inventors, and its physicochemical properties, production process and pharmacological activities are disclosed in detail in a Japanese Laid Open Patent Publication (JP-A-6-157582).

The production of said compound can be carried out, for example, by means of Penicillium sp. F-31405, as disclosed in JP-A-6-157582, or by means of a microorganism such as Penicillium sp. F31405-17M which is a mutant of said strain and which is excellent in the production of said compound.

Penicillium sp. F31405-17M has the following mycological characteristics.

(1) Morphology

The configuration of F31405-17M strain is the same as the original strain Penicillium sp. F-31405. Namely, conidiophores are 110 to 210×1.8 to 3.6 μm and have a smooth surface or fine projections. Further, they form symmetrical double verticillate penicilli. Metulae are 10.0 to 13.1×2.3 to 3.1 μm, and from 4 to 8 metulae fasciculate. Phialides are (9.7 to) 11.4 to 15.0×1.8 to 2.6 μm and verticillate. Conidia have a smooth surface and are subspherical to oval or egg shaped, and their sizes are 3.5 to 4.4×2.6 to 3.5 μm.

(2) Culture characteristics

The culture characteristics of F31405-17M strain are slightly different from the original strain F-31405. The growth characteristics when it was cultured at 25° C. for 7 days using various agar media, are shown in Table 1. In the Table, the colors were designated based on the names of colors in Methuen Handbook of Color, 3rd ed., 1984.

TABLE 1

Growth characteristics of F31405-17M strain

| Culture media | Diameter of colony (mm) | Color of colony | Color of the colony reverse | Colony texture |
|---|---|---|---|---|
| Czapek agar | 13 to 15 | Pale green to grayish green | Pale green to grayish green | Slightly velutinous |
| Czapek yeast extract agar | 17 to 20 | Yellowish white to dark green | Bright yellow to yellowish white | Slightly velutinous |
| Malt extract agar | 30 to 32 | Dark green | Yellowish gray to yellowish white | Velutinous |

On each culture medium, formation of conidia is good, and it is particularly good in a malt extract agar medium. No secrete is observed. On a Czapek agar medium and a czapek yeast extract agar medium, a bright yellow soluble pigment is produced. With the original Penicillium sp. F-31405, a premature sclerotium tissue may sometimes be formed during the culturing at 37° C. However, no such a tissue is observed with the improved F31405-17M strain.

Further, in each culture medium, the growth at 37° C. is poor than the growth at 25° C. This strain can be grown within a range of from 12 to 37° C., and the optimum growth temperature is 28.5° C. Further, it can be grown within a range of from pH 2 to pH 11, and the optimum pH is in the vicinity of 6.5.

Further, both strains of Penicillium sp. F-31405 and F31405-17M are deposited as international depositions at National Institute of Bioscience and Human-Technology (NIBH), Agency of Industrial Science and Technology, Ministry of International Trade and Industry (address: 1–3, Higashi 1-chome, Tsukuba-shi, Ibaraki-ken 305, Japan), and the deposition numbers are FERM BP-5714 (date of original deposition: Oct. 20, 1992) and FERM BP-5716 (date of original deposition: Sep. 13, 1996), respectively.

Among the compounds represented by the general formula (I), a compound wherein R is a lower alkyl group, can be readily produced and made available by removing an acetyl group of BE-31405 and then introducing a lower alkyl group to the compound, by a method well-known in the chemical field. In such a case, it is preferred to carry out the reaction after properly protecting a carboxyl group and a hydroxyl group in the compound as the case requires and then remove the protective groups.

Especially, among the compounds represented by the general formula (I), a compound wherein R is methyl group, is a compound disclosed in J.Antibiotics, vol.48, 1171–1172 (1995), and this compound can be produced and made available by a method disclosed in this literature.

The azole type antifungal agent is a compound having antifungal activities and represents a compound having an imidazole ring or a triazole ring in its molecule, and it may, for example, be one or more selected from antifungal agents such as butoconazole or oxiconazole, clotrimazole, terconazole, econazole, tioconazole, miconazole, fluconazole, ketoconazole and itraconazole, disclosed in a literature such as Clinical Infectious Diseases, vol.14 (Suppl 1), S161-9 (1992). Among them, miconazole, furconazole or itraconazole is, for example, preferred. These pharmaceutical agents may be commercial products or may be produced and made available in accordance with the above-mentioned literature.

Effects of the combined use of BE-31405 and the azole type antifunaal agent (antifungal activities)

The minimum inhibitory concentration (MIC, by an agar dilution method) of miconazole against *Candida albicans* IFO 1385 in the presence or absence of BE-31405, is shown in Table 2.

TABLE 2

| BE-31405 ($\mu$g/ml)[a] | MIC of miconazole ($\mu$g/ml)[b] |
|---|---|
| 0.0 | 12.5 |
| 0.1 | 1.56 |
| 0.2 | 0.78 |
| 0.39 | 0.39 |
| 0.78 | 0.05 |

[a]: MIC with BE-31405 alone under this test condition, was 1.56 $\mu$g/ml.
[b]: Measured after culturing at 37° C. for 2 days on a yeast morphology agar, manufactured by Difico Co.

As shown in Table 2, the antifungal activities of miconazole is substantially enhanced in the presence of a low concentration of BE-31405. It has been made clear that this effect is a synergistic effect, as the fractional inhibitory concentration index is calculated to be 0.2.

Now, the minimum inhibitory concentrations (MIC, by an agar dilution method) of itraconazole against *Candida albi-cans* IFO 1270, IFO 1385 and ATCC90028 in the presence and absence of BE-31405, are shown in Tables 3, 4 and 5, respectively. As the agar medium for the measurement of MIC, a culture medium having 1% of glucose and 1.2% of agar added to a yeast nitrogen base, manufactured by Difico Co., was used, and after inoculation of the strain solution, culturing was carried out at 37° C. for 2 days, whereupon the concentration at which no growth of the strain was observed, was judged to be MIC.

TABLE 3

Effect of combined use against *Candida albicans* IFO 1270

| BE-31405 ($\mu$g/ml)[a] | MIC of intraconazole ($\mu$g/ml) |
|---|---|
| 0.0 | >100 |
| 0.006 | 0.05 |
| 0.025 | 0.013 |
| 0.1 | 0.013 |
| 0.39 | 0.013 |

[a]: MIC with BE-31405 alone under this test condition, was 0.78 $\mu$g/ml.

TABLE 4

Effect of combined use against *Candida albicans* IFO 1385

| BE-31405 ($\mu$g/ml)[a] | MIC of intraconazole ($\mu$g/ml) |
|---|---|
| 0.0 | >100 |
| 0.025 | 1.56 |
| 0.05 | 0.2 |
| 0.1 | 0.1 |
| 0.39 | 0.05 |

[a]: MIC with BE-31405 alone under this test condition, was 1.56 $\mu$g/ml.

TABLE 5

Effect of combined use against *Candida albicans* ATCC 90028

| BE-31405 ($\mu$g/ml)[a] | MIC of intraconazole ($\mu$g/ml) |
|---|---|
| 0.0 | >100 |
| 0.025 | 1.56 |
| 0.05 | 0.2 |
| 0.1 | 0.2 |
| 0.39 | 0.1 |

[a]: MIC with BE-31405 alone under this test condition, was 1.56 $\mu$g/ml.

As shown in Tables 3, 4 and 5, the antifungal activities of itraconazole are substantially enhanced in the presence of a low concentration of BE-31405. It has been made clear that these effects are strong synergistic effects, as the fractional inhibitory concentration indices are calculated to be at most 0.2.

As a result of the foregoing, it has been found that by the combined use of BE-31405 and an azole type antifungal agent, the antifungal activities of both agents are synergistically enhanced, and they are effective against various destructive fungi and resistant strains. Accordingly, the antifungal composition of the present invention is very useful as an antifungal agent.

The antifungal composition of the present invention can be administered orally or parenterally in its clinical application, and it may be formulated to meet the administration mode by adding pharmacologically acceptable various additives, as the case requires, and used as an antifungal agent.

The form for such formulation may, for example, be solid formulations such as tablets, capsules, granules, pills, troches, powders or suppositories, or liquid formulations such as syrups, elixirs, suspensions or injections, as well as aerosols, eyedrops, ointments, ophthalmic ointments, emulsions, creams, liniments or lotions. These formulations may be prepared in accordance with conventional methods commonly used in the field of drug formulations.

As the additives, various additives which are commonly used in the drug formulation field, can be used. For example, saccharides such as lactose or glucose, a starch such as corn, wheat or rice, a vegetable oil such as soybean oil, peanuts oil or sesame oil, a fatty acid such as stearic acid, an inorganic salt such as magnesium metasilicate aluminate or anhydrous calcium phosphate, a synthetic polymer such as polyvinylpyrrolidone or polyalkylene glycol, a fatty acid salt such as calcium stearate or magnesium stearate, an alcohol such as stearyl alcohol or benzyl alcohol, a synthetic cellulose derivative such as methyl cellulose, carboxymethyl cellulose, ethyl cellulose or hydroxy-propylmethyl cellulose, or others such as water, gelatin, talc and gum arabic, may, for example, be mentioned.

Further, in the case of a liquid formulation, it may be in such a form that at the time of use, it is dissolved or suspended in water or in other suitable medium. Especially when administration is carried out by e.g. intramuscular injection, intravenous injection or subcutaneous injection, a suitable medium for such an injection may, for example, be distilled water for injection, a hydrochloric acid lidocaine aqueous solution (for intramuscular injection), physiological saline, an aqueous glucose solution, ethanol, liquid for intravenous injection (such as an aqueous solution of citric acid and sodium citrate) or an electrolyte solution (for intravenous drip and intravenous injection), or a mixed solution thereof. Further, a buffer or a preservative may be added.

These formulations may contain usually from 0.1 to 100 wt %, preferably from 5 to 100 wt %, of the active ingredient in the case of the above-mentioned solid formulations, and may contain from 0.1 to 10 wt %, preferably from 1 to 5 wt %, in the case of other formulations.

Further, the weight ratio of the compound represented by the general formula (I) or its pharmaceutically acceptable salt to the azole type antifungal agent, may be from 0.001:1 to 1000:1. Particularly preferably, the weight ratio is from 0.05:1 to 20:1.

A practically preferred dose of the antifungal composition of the present invention varies depending upon the type of the compound used, the type of the composition blended, the sex, age, weight, diseased degree and the particular section to be treated of the patient, but it is usually from 0.1 to 100 mg/kg in the case of oral administration and from 0.01 to 100 mg/kg in the case of parenteral administration, per adult per day. The number of times of administration varies depending upon the administration method and the symptom, but it is preferred to carry out the administration from one to five times per day.

BEST MODE FOR CARRYING OUT THE INVENTION

Now, the present invention will be described in further detail with reference to Examples, Preparation Examples and Reference Examples, but the present invention is by no means thereby restricted.

EXAMPLE 1

5 Parts of BE-31405, 5 parts of miconazole, 15 parts of heavy magnesium oxide and 75 parts of lactose were uniformly mixed to obtain a powdery or fine granular powder of at most 350 μm. This powder was put into a capsule container to obtain a capsule.

EXAMPLE 2

35 parts of BE-31405, 10 parts of miconazole, 15 parts of starch, 16 parts of lactose, 21 parts of crystalline cellulose and 30 parts of polydistilled water were uniformly mixed, then pulverized and granulated, and dried, and then sieved to obtain granules having a size of from 1410 to 177 μm in diameter.

EXAMPLE 3

Granules were prepared in the same manner as in Example 2, and then 3 parts of calcium stearate was added to 96 parts of the granules, followed by compression molding to obtain tablets having a diameter of 10 mm.

EXAMPLE 4

10 parts of crystalline cellulose and 3 parts of calcium stearate were added to 90 parts of the granules obtained by the method of Example 2, followed by compression molding to obtain tablets having a diameter of 8 mm. Then, a mixed suspension of syrup gelatin and precipitated calcium carbonate, was added thereto to prepare sugar-coated tablets.

EXAMPLE 5

0.3 Part of BE-31405, 0.3 part of miconazole, 2.4 parts of a nonionic surfactant and 97 parts of physiological saline were heated and mixed, and then put in an ampule, followed by sterilization to prepare an injection.

EXAMPLE 6

0.5 part of BE-31405, 0.5 part of miconazole, 49.5 parts of Macrogol 4000 and 49.5 parts of Macrogol 400 were mixed and well kneaded to be homogenous, thereby to obtain an ointment.

PREPARATION EXAMPLE 1

Preparation of BE-31405

Fungus F-31405 strain cultured on a slant agar medium was inoculated into four Erlenmeyer flasks having a capacity of 500 ml containing 110 ml of a culture medium (pH 6.0 before sterilization) comprising 0.3% of polypeptone, 1% of glucose, 1.0% of wheat embryo, 0.5% of gluten meal, 0.3% of maltextract, 3.0% of maltose, 0.2% of sodium chloride, 0.1% of sodium nitrate, 0.1% of monopotassium phosphate, 0.05% of magnesium sulfate, 0.0002% of ferrous sulfate, 0.00004% of cupric chloride, 0.00004% of manganese chloride, 0.00004% of cobalt chloride, 0.00008% of zinc sulfate, 0.00008% of sodium borate and 0.00024% of ammonium molybdate, and cultured on a rotary shaker (180 rpm) at 28° C. for 72 hours. 2 ml each of this culture solution was inoculated to 50 Erlenmeyer flasks having a capacity of 500 ml containing 110 ml of the above culture medium, and cultured on a rotary shaker (180 rpm) at 28° C. for 72 hours.

The culture solution (about 5 lit.) obtained by culturing was subjected to heat sterilization at 90° C. for 10 minutes and then filtered. The culture filtrate was adsorbed on a 1.2 lit. diaion HP-20 column. After washing with 30% methanol (4 lit.), the active component was eluted with 3 lit. of methanol. The methanol eluate was concentrated under reduced pressure, and water was added to 500 ml. The mixture was extracted twice with 500 ml ethyl acetate, and the obtained ethyl acetate extract solution was concentrated under reduced pressure to dryness. This crude substance was subjected to silica gel column chromatography (inner diameter: 2 cm, length 30 cm, Kieselgel 60, Merck Co.), and sequentially eluted with 400 ml (100:1) and 800 ml (50:1) of a solvent mixture of chloroform/methanol. The fraction containing BE-31405 was concentrated under reduced pressure to dryness to obtain 320 mg of a crude substance. Then, this crude substance was subjected to reversed phase HPLC [Chromatorex-OSD (100 Å-5 µm), 20Φ×250 mm, Fuji Davison Chemical Co.] using 70% methanol water as a mobile layer, whereby a peak in the vicinity of 22 minutes at UV220 nm at a flow rate of 9 ml/min, was collected and concentrated under reduced pressure to dryness. The obtained crude BE-31405 was subjected to Sefadex LH20 column chromatography (inner diameter: 1.5 cm, length: 90 cm) using methanol as an eluent, and the fraction containing pure BE-31405 was concentrated under reduced pressure to dryness to obtain 103.4 mg of BE-31405 as white solid.

A method for producing BE-31405 using Penicillium sp. F31405-17M will be shown in Reference Examples.

The conditions for separation and quantitative analysis of BE-31405 in the high performance liquid chromatography (HPLC) used in Reference Examples, are as follows.
HPLC conditions
 Column: YMC Pack ODS-A 250×4.6 mm I.D.
 Column temperature: 40° C.
 Mobile phase: 10% acetonitrile (containing 0.0375% of Trifluoroacetic acid)/80% acetonitrile (containing 0.025% of trifluoroacetic acid)=55/45
 Retention time: 17 minutes
 Flow rate: 1.2 ml/min
 Detection: 220 nm

REFERENCE EXAMPLE 1

Spores of Penicillium sp. F-31405 strain cultured on a slant agar medium (pH 5.6 before sterilization) comprising 0.2% of potato extract, 1% of glucose and 1.5% of agar, were suspended in 10 ml of sterilized water, and solutions diluted 10, 100, 1000, 10000 and 100000 times with sterilized water, were prepared. 0.2 ml of each of the diluted solutions was spread on a plate agar medium having the above composition and cultured at 25° C. for 4 days, whereupon the grown colony was transplanted to a slant agar medium and cultured at 25° C. for 14 days to obtain a single spore isolated strain F31405-17M of Penicillium sp. F-31405. The single spore isolated strain F31405-17M cultured on the slant agar medium was inoculated to one Erlenmeyer flask having a capacity of 500 ml containing 110 ml of a Czapek-Dox medium (pH 6.0 before sterilization) comprising 3.6% of glucose, 0.2% of sodium nitrate, 0.1% of dipotassium phosphate, 0.05% of magnesium sulfate, 0.05% of potassium chloride and 0.001% of ferrous sulfate, and cultured on a rotary shaker (180 rpm) at 28° C. for 72 hours. 2 ml of this culture solution was inoculated to one Erlenmeyer flask having a capacity of 500 ml containing 110 ml of a modified medium A (pH 6.0 before sterilization) comprising 7.2% of glucose, 0.2% of sodium nitrate, 0.1% of dipotassium phosphate, 0.1% of magnesium sulfate, 0.05% of potassium chloride, 2% of yeast extract and 0.5% of nicotinic acid, and cultured on a rotary shaker (180 rpm) at 28° C. for 168 hours. 15 ml of the culture solution was taken, and 15 ml of ethyl acetate was added, followed by stirring for 30 minutes for extraction. 10 ml of the ethyl acetate layer was taken, and ethyl acetate was distilled off under reduced pressure, and the residue was dissolved in 1 ml of methanol. The concentration of BE-31405 in this methanol solution was measured by a high performance liquid chromatography. As a result, the concentration of BE-31405 per 1 ml of the culture solution was 100 µg.

REFERENCE EXAMPLE 2

The single spore isolated strain F31405-17M of Penicillium sp. F-31405 strain cultured on a slant agar medium, was inoculated into two Erlenmeyer flasks having a capacity of 500 ml containing 110 ml of a modified medium B (pH 6.0 before sterilization) comprising 7.2% of glucose, 0.2% of sodium nitrate, 0.1% of dipotassium phosphate, 0.1% of magnesium sulfate and 0.05% of potassium chloride, and cultured on a rotary shaker (180 rpm) at 28° C. for 72 hours. 200 ml of this culture solution was inoculated into one fermentation tank having a capacity of 20 lit. containing 10 lit. of a modified medium C (pH 6.0 before sterilization) comprising 7.2% of glucose, 0.1% of magnesium sulfate, 2% of yeast extract and 0.2% of nicotinic acid, and cultured at 28° C. for 9 days with stirring (300 rpm) under supplying air (20 lit. per minute). 15 ml of the culture solution was taken, and 15 ml of ethyl acetate was added thereto, followed by stirring for 30 minutes for extraction. 10 ml of the ethyl acetate layer was taken, and ethyl acetate was distilled off under reduced pressure, and the residue was dissolved in 1 ml of methanol. The concentration of BE-31405 in this methanol solution was measured by a high performance liquid chromatography. As a result, the concentration of BE-31405 per 1 ml of the culture solution was 50 µg.

INDUSTRIAL APPLICABILITY

The antifungal composition of the present invention exhibits excellent antifungal activities and thus is useful as an antifungal agent.

What is claimed is:
1. An antifungal composition, comprising a synergistic mixture, comprising a compound having the formula (I):

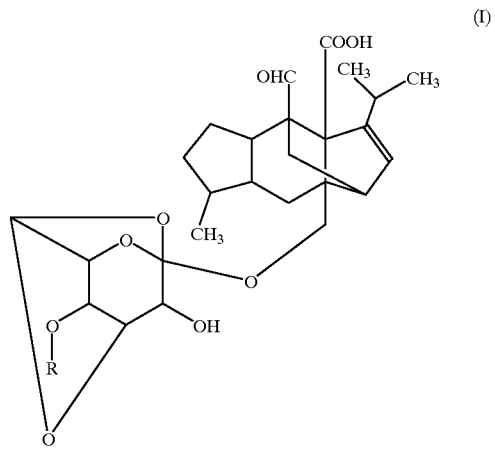

wherein R is acetyl or alkyl; or a pharmaceutically acceptable salt thereof, and an azole antifungal agent selected from the group consisting of an imidazole compound and a triazole compound, as active ingredients.

2. The antifungal composition of claim 1, wherein R is acetyl.

3. The antifungal composition of claim 1, wherein R is alkyl.

4. The antifungal composition of claim 3, wherein said alkyl is $C_1$–$C_6$ linear or branched alkyl.

5. The antifungal composition of claim 4, wherein said $C_1$–$C_6$ linear or branched alkyl is selected from the group consisting of methyl, ethyl, propyl, isopropyl, butyl, sec-butyl, tert-butyl, pentyl and hexyl.

6. The antifungal composition of claim 1, wherein said pharmaceutically acceptable salt is a base-addition salt selected from the group consisting of an alkali metal salt, alkaline earth metal salt, ammonium salt, and organic amine salt.

7. The antifungal composition of claim 1, wherein the azole antifungal agent is selected from the group consisting of butoconazole, oxiconazole, clotrimazole, terconazole, econazole, tioconazole, miconazole, fluconazole, ketoconazole and itraconazole.

8. The antifungal composition of claim 1, wherein the weight ratio of the compound of the formula (I) and the azole antifungal agent is from about 0.001:1 to 1000:1.

9. The antifungal composition of claim 1, further comprising a carrier, which is in a form selected from tablets, capsules, granules, troches, powders, pills, suppositories, syrups, elixirs, suspensions, aerosls, eyedrops, ointments, opthalmic ointments, emulsions, creams, liniments or lotions.

10. The antifungal composition of claim 1, which is in a form suitable for injection.

* * * * *